US009956203B2

(12) United States Patent
Ozaki et al.

(10) Patent No.: US 9,956,203 B2
(45) Date of Patent: May 1, 2018

(54) PLASTIC CONTAINER COMPRISING CYCLIC POLYOLEFIN LAYER

(75) Inventors: Kazuhiko Ozaki, Osaka (JP);
Munetomo Matsuda, Osaka (JP);
Tetsurou Nishimura, Osaka (JP);
Kenjiro Takayanagi, Yokkaichi (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days. days.

(21) Appl. No.: 12/955,776

(22) Filed: Nov. 29, 2010

(65) Prior Publication Data

US 2011/0068037 A1 Mar. 24, 2011

Related U.S. Application Data

(63) Continuation of application No. 12/744,208, filed as application No. PCT/JP2008/071197 on Nov. 21, 2008, now abandoned.

(30) Foreign Application Priority Data

Nov. 22, 2007 (JP) .................................. 2007-303568

(51) Int. Cl.
*B65D 1/40* (2006.01)
*A61K 31/4152* (2006.01)
*B32B 27/32* (2006.01)
*B32B 27/08* (2006.01)
*B32B 27/30* (2006.01)
*A61J 1/10* (2006.01)
*A61K 9/00* (2006.01)

(52) U.S. Cl.
CPC .......... *A61K 31/4152* (2013.01); *B32B 27/08* (2013.01); *B32B 27/302* (2013.01); *B32B 27/32* (2013.01); *B32B 27/325* (2013.01); *A61J 1/10* (2013.01); *A61K 9/0019* (2013.01); *B32B 2250/24* (2013.01); *B32B 2270/00* (2013.01); *B32B 2307/30* (2013.01); *B32B 2307/308* (2013.01); *B32B 2307/31* (2013.01); *B32B 2307/412* (2013.01); *B32B 2307/50* (2013.01); *B32B 2307/51* (2013.01); *B32B 2307/546* (2013.01); *B32B 2307/558* (2013.01); *B32B 2307/7242* (2013.01); *B32B 2307/7265* (2013.01); *B32B 2439/80* (2013.01); *Y10T 428/2826* (2015.01)

(58) Field of Classification Search
CPC .. A61K 9/0012; A61K 9/0019; A61K 31/415; A61K 31/4152; Y10T 428/1352; Y10T 428/1359; Y10T 428/139; B32B 27/325; A61J 1/05; A61J 1/10
USPC ........ 428/34.1, 34.2, 34.3, 35.2, 35, 7, 35.9, 428/36.6, 213, 347, 474.4, 477.7, 480, 428/483, 500, 515; 383/105, 109; 604/403–416; 426/72, 73, 167; 206/524.2, 660; 220/660
See application file for complete search history.

(56) References Cited

U.S. PATENT DOCUMENTS

| 4,311,810 | A | * | 1/1982 | Fujii et al. ..................... 525/321 |
| 5,486,415 | A | * | 1/1996 | Kimura et al. ................ 428/349 |
| 5,539,056 | A | * | 7/1996 | Yang et al. .................... 525/240 |
| 6,451,227 | B1 | * | 9/2002 | Greshes ........... B29D 11/00413 264/2.4 |
| 6,572,603 | B1 | | 6/2003 | Tani et al. |
| 7,105,604 | B2 | | 9/2006 | Shimizu et al. |
| 7,259,845 | B2 | * | 8/2007 | Dietz ..................... B01L 3/5025 356/246 |
| 8,029,885 | B2 | | 10/2011 | Manabe et al. |
| 2002/0040100 | A1 | * | 4/2002 | Kume et al. ..................... 525/89 |
| 2004/0043238 | A1 | * | 3/2004 | Wuest et al. .................. 428/515 |
| 2004/0075039 | A1 | * | 4/2004 | Dubey ............. B29D 11/00432 249/134 |
| 2004/0137177 | A1 | | 7/2004 | Saito et al. |
| 2005/0031812 | A1 | * | 2/2005 | Suzuki ......................... 428/35.2 |
| 2005/0075611 | A1 | * | 4/2005 | Hetzler ................. A61L 2/0011 604/192 |
| 2005/0208240 | A1 | * | 9/2005 | Manabe et al. .............. 428/35.7 |

(Continued)

FOREIGN PATENT DOCUMENTS

| CN | 1652935 A | 8/2005 |
| CN | 1824701 A | 8/2006 |

(Continued)

OTHER PUBLICATIONS

Zeonor 1060R product data sheet, Zeon Chemicals, Aug. 19, 2003.*
Mitsubishi Chemicals "Mitsubishi Chemicals Performance Polymers—Zelas Overview", Jul. 2 and 3, 2007, Archived at http://web.archive.org/web/20070702003908/http://www.mcc-spd.com/en/product/zelas/zelas.html.*
TOPAS Advanced Polymers "Topas 9506F-04 Data Sheet", Aug. 30, 2006. available at http://www.topas.com/sites/default/filed/tds_9506f_04_e_2006.pdf.*

(Continued)

*Primary Examiner* — Lee E Sanderson
(74) *Attorney, Agent, or Firm* — Locke Lord LLP; Bryan D. Zerhusen; Nicholas J. DiCeglie, Jr.

(57) ABSTRACT

The present invention provides and a plastic container and multilayered films, which comprises a heat-sealable seal layer, a cyclic polyolefin layer, and an outermost layer, wherein the seal layer comprises polypropylene, the cyclic polyolefin layer comprises a cyclic polyolefin polymer or a cyclic polyolefin copolymer, and the outermost layer comprises a layer containing polypropylene, and which further comprises a resin composition layer comprises a blended product of a propylene polymer and a styrene elastomer. The plastic container of the present invention can suppresses a reduction in the medicament content of a liquid-state medicament and is excellent in terms of shock resistance, handling ability during the filling of the container with the medicament, and the moldability and transparency of the container.

12 Claims, No Drawings

(56) References Cited

U.S. PATENT DOCUMENTS

| | | | |
|---|---|---|---|
| 2006/0270794 A1 | 11/2006 | Fumihiko et al. | |
| 2007/0142557 A1* | 6/2007 | Karsten et al. | 525/240 |
| 2007/0237916 A1* | 10/2007 | Rasmussen et al. | 428/35.2 |
| 2007/0279395 A1* | 12/2007 | Philipp | G01R 27/2605 345/173 |
| 2008/0063825 A1* | 3/2008 | Mori et al. | 428/36.6 |
| 2008/0246496 A1* | 10/2008 | Hristov | G06F 3/044 324/686 |
| 2009/0023827 A1* | 1/2009 | Lendlein | C08J 3/28 521/143 |
| 2009/0208685 A1* | 8/2009 | Rivers | B32B 15/08 428/36.91 |
| 2009/0230575 A1* | 9/2009 | Liu | B29C 33/40 264/1.1 |
| 2010/0075081 A1 | 3/2010 | Manabe et al. | |
| 2010/0163446 A1 | 7/2010 | Suzuki et al. | |
| 2010/0270794 A1 | 10/2010 | Manabe et al. | |

FOREIGN PATENT DOCUMENTS

| | | |
|---|---|---|
| CN | 1926186 | 3/2007 |
| CN | 101044021 A | 9/2007 |
| EP | 0208874 A1 | 1/1987 |
| EP | 524802 A1 | 1/1993 |
| EP | 1053737 A1 | 11/2000 |
| EP | 1106647 A2 | 6/2001 |
| EP | 1394071 A1 | 3/2004 |
| EP | 1471085 A1 | 10/2004 |
| EP | 1602350 A1 | 12/2005 |
| EP | 1803552 A1 | 7/2007 |
| EP | 2033615 A1 | 3/2009 |
| JP | 3215425 A | 9/1991 |
| JP | 531523 B | 5/1993 |
| JP | 535128 B | 5/1993 |
| JP | 5293159 A | 11/1993 |
| JP | 07-164604 A | 6/1995 |
| JP | 2001-030425 A | 2/2001 |
| JP | 2001172454 A | 6/2001 |
| JP | 2001226435 A | 8/2001 |
| JP | 3215426 B2 | 10/2001 |
| JP | 2002301796 A | 10/2002 |
| JP | 2003-052791 A | 2/2003 |
| JP | 2003292700 A | 10/2003 |
| JP | 2004-188039 A | 7/2004 |
| JP | 2004188039 A * | 7/2004 |
| JP | 2004196337 A | 7/2004 |
| JP | 2003-24415 A | 8/2004 |
| JP | 2005525952 T | 9/2005 |
| WO | 1999/039679 A1 | 8/1999 |
| WO | 03097355 A1 | 11/2003 |
| WO | WO-03/097739 | 11/2003 |
| WO | WO-2005/075558 | 8/2005 |
| WO | 2006/043459 A1 | 4/2006 |
| WO | WO 2006043459 A1 * | 4/2006 |
| WO | 200755312 A1 | 5/2007 |

OTHER PUBLICATIONS

The TOPAS Cyclic Olefin Copolymer—Packaging catalog from TOPAS Advanced Polymers, Polyplastic Co. https://www.polyplastics.com/en/product/lines/topas/packaging_e.pd.*
Jan H. Schut, New Cyclic Olefin, Plastics Technology, Mar. 2000, avialable online at http://www.ptonline.com/articles/new-cyclic-olefins.*
Zeon Coproration, ZEONOR Basic Propertires, archived at https://web.archive.org/web/20050318063242/http://www.zeon.co.jp/business_e/enterprise/speplast/speplast2_9.html on Mar. 18, 2005.*
Vaccari, John. Materials Handbook. McGraw-Hill Publishing, 2002, p. 658.*
Shin et al., Chemical Structure and Physical Properties of Cyclic Olefin Copolymers, Pure and Applied Chemistry, IUPAC, vol. 77, No. 5 p. 803.*
Supplementary European Search Report issued in EP 088512340.3.
European Search Report issued in EP 10008573.7.
Form PCT/ISA/237, Written Opinion for PCT/JP2008/071197.
Form PCT/ISA/210, International Search Report for PCT/JP2008/071197.
Kawai et al., "Effects of a Nobel Free Radical Scavenger, MCI-186, on Ischemic Brain Damage in the Rat Distal Middle Cerebral Artery Occlusion Model", The Journal of Pharmacology and Experiemental Therapeutics, vol. 921, pp. 921-927 (1997).
Wu Tai-Wing et al., "MCI-186: further histochemical and biochemical evidence of neuroprotection", Life Sciences 67, pp. 2387-2392, Elsevier Science Inc. (2000).
FORM PCT/ISA/237, WO, Jan. 27, 2009, Writtten Opinion for PCT/JP2008/071197.
FORM PCT/ISA/210, WO, Jan. 27, 2009, ISR for PCT/JP2008/071197.
Office Action issued in Chinese application No. 201010526527.X.
Official Action dated Jan. 8, 2013 issued in corresponding Japanese Patent Application No. 2009-542592 with English Language translation thereof.
Office Action dated Jul. 17, 2013, in corresponding Taiwanese Patent Application No. 099137935 (and English translation).
Office Action dated Jul. 8, 2013, in corresponding Chinese Patent Application No. 201010526527.X (and English translation).
Japanese Office Action dated May 14, 2013 in corresponding Japanese Patent Application No. 2009-542592 (with partial English translation).
Official Action dated Aug. 28, 2013 in corresponding Taiwanese Patent Application No. 097145184 and (English translation).
Official Action dated Sep. 26, 2013 in corresponding European Patent Application No. 10 008 573.7.
Office Action dated Apr. 3, 2014 in corresponding Chinese Patent Application No. 201010526527.X.

* cited by examiner

PLASTIC CONTAINER COMPRISING CYCLIC POLYOLEFIN LAYER

This application is a continuation of U.S. application Ser. No. 12/744,208, filed Sep. 1, 2010, which is the U.S. National Phase of PCT international application Ser. No. PCT/JP2008/071197, filed Nov. 21, 2008, designating the United States and published in Japanese on May 28, 2009 as publication WO 2009/066752 A1, which claims priority to Japanese application Ser. No. 2007-303568, filed Nov. 22, 2007. The entire contents of the aforementioned patent applications are incorporated herein by this reference.

TECHNICAL FIELD

The present invention relates to a plastic container suitable for containing a liquid-state medicament and a multilayered film used for this container.

BACKGROUND ART

A reduction in the content of a certain kind of medicament is suppressed using a container composed of cyclic polyolefin. The suppression of a reduction in the content of a certain kind of medicament is disclosed in JP Patent Publication (Kokai) No. 5-293159 A (1993) (Patent Document 1) and JP Patent Publication (Kokai) No. 2003-24415 A (Patent Document 2), for example. However, cyclic polyolefin is rigid and fragile, and further, it is poor in terms of heat-sealing properties. Thus, cyclic polyolefin has been problematic in that a practical bag cannot be directly formed with the cyclic polyolefin itself. In order to solve this problem, JP Patent Publication (Kokai) No. 2002-301796 A (Patent Document 3) and JP Patent Publication (Kohyo) No. 2005-525952 A (Patent Document 4), for example, have proposed a multilayered film comprising a specific ethylene-α-olefin copolymer and cyclic polyolefin and a container constituted with the same.

Moreover, if a constituted multilayered film is rigid and inflexible, it causes problems such as low shock resistance and poor handling ability during the filling of a container with a medicament.

On the other hand, it has been known that a pyrazolone derivative represented by the formula (I) as shown below has, as a medical use, an action to normalize brain function (Patent Document 5; JP Patent Publication (Kokoku) No. 5-31523 B (1993)), an action to suppress generation of lipid peroxide (Patent Document 6; JP Patent Publication (Kokoku) No. 5-35128 B (1993); the compound of Example 1), an antiulcer action (Patent Document 7; JP Patent Publication (Kokai) No. 3-215425 A (1991)), an action to suppress an increase in blood sugar (Patent Document 8; JP Patent Publication (Kokai) No. 3-215426 A (1991)), and the like:

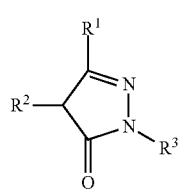

(I)

(wherein $R^1$ represents a hydrogen atom, an aryl, an alkyl containing 1 to 5 carbon atoms, or an alkoxycarbonylalkyl containing 3 to 6 carbon atoms in total; $R^2$ represents a hydrogen atom, an aryloxy, an arylmercapto, an alkyl containing 1 to 5 carbon atoms, or a hydroxyalkyl containing 1 to 3 carbon atoms; or $R^1$ and $R^2$ together represent an alkylene containing 3 to 5 carbon atoms; $R^3$ represents a hydrogen atom, an alkyl containing 1 to 5 carbon atoms, a cycloalkyl containing 5 to 7 carbon atoms, a hydroxyalkyl containing 1 to 3 carbon atoms, a benzyl, naphthyl or phenyl, or a phenyl substituted with 1 to 3 identical or different substituents selected from the group consisting of an alkoxy containing 1 to 5 carbon atoms, a hydroxyalkyl containing 1 to 3 carbon atoms, an alkoxycarbonyl containing 2 to 5 carbon atoms in total, an alkylmercapto containing 1 to 3 carbon atoms, an alkylamino containing 1 to 4 carbon atoms, a dialkylamino containing 2 to 8 carbon atoms in total, a halogen atom, a trifluoromethyl, a carboxyl, a cyano, a hydroxyl group, a nitro, an amino, and an acetamide).

Moreover, since June 2001, the compound represented by the formula (I) has been commercially available as a brain-protecting agent (generic name: "Edaravone"; product name: "Radicut"; manufactured and distributed by Mitsubishi Tanabe Pharma Corporation). This "Edaravone" has been reported to have high reactivity with active oxygen (Non-Patent Documents 1 and 2). Thus, Edaravone is a free radical scavenger that acts to scavenge various types of free radicals including active oxygen as a typical example, so as to prevent cell injury.

At present, Radicut is commercially available as a Radicut injection 30 mg in the form of a 20 ml of solution containing 30 mg of 3-methyl-1-phenyl-2-pyrazoline-5-one (Edaravone) filled into a glass ampule. Furthermore, International Publication WO2007/55312 (Patent Document 9) reports a plastic container filled with an aqueous solution containing Edaravone, coloration of which is suppressed. However, a plastic container capable of suppressing a reduction in the content of Edaravone due to adhesion of Edaravone to the plastic container has not yet been disclosed.

[Patent Document 1] JP Patent Publication (Kokai) No. 5-293159 A (1993)
[Patent Document 2] JP Patent Publication (Kokai) No. 2003-24415 A
[Patent Document 3] JP Patent Publication (Kokai) No. 2002-301796 A
[Patent Document 4] JP Patent Publication (Kohyo) No. 2005-525952 A
[Patent Document 5] JP Patent Publication (Kokoku) No. 5-31523 B (1993)
[Patent Document 6] JP Patent Publication (Kokoku) No. 5-35128 B (1993)
[Patent Document 7] JP Patent Publication (Kokai) No. 3-215425 A (1991)
[Patent Document 8] JP Patent Publication (Kokai) No. 3-215426 A (1991)
[Non-Patent Document 1] Kawai, H., et al., J. Pharmacol. Exp. Ther., 281(2), 921, 1997
[Non-Patent Document 2] Wu, T W. et al., 67(19), 2387, 2000
[Patent Document 9] International Publication WO2007/55312

DISCLOSURE OF THE INVENTION

Problems to be Solved by the Invention

It is an object of the present invention to provide a plastic container which suppresses a reduction in the content of a liquid-state medicament and is excellent in terms of shock resistance, handling ability during the filling of the container with the medicament, and the moldability and transparency of the container, and a multilayered film used for the aforementioned container.

Means for Solving the Problems

The multilayered film of the present invention for achieving the aforementioned object comprises a heat-sealable seal layer, a cyclic polyolefin layer, and an outermost layer, wherein the seal layer comprises polypropylene, the cyclic polyolefin layer comprises a cyclic polyolefin polymer or a cyclic polyolefin copolymer, and the outermost layer comprises a layer containing polypropylene, and the present multilayered film further comprises a resin composition layer comprising a blended product of a propylene polymer and a styrene elastomer. However, the multilayered film of the present invention excludes a five-layered plastic film only composed of a seal layer-an adhesive layer-a barrier layer-an adhesive layer-a material layer, wherein each of the seal layer and the material layer consists of only a polypropylene elastomer having a melting point of 165° C., each of the adhesive layers consists of only MODIC manufactured by Mitsubishi Chemical Corporation, and the barrier layer consists of only a cyclic polyolefin polymer having a glass transition temperature of 136° C.

Moreover, the plastic container according to the present invention for achieving the aforementioned object is molded by heat-sealing the peripheral portions of the multilayered films which comprise a heat-sealable seal layer, a cyclic polyolefin layer, and an outermost layer wherein the seal layer comprises polypropylene, the cyclic polyolefin layer comprises a cyclic polyolefin polymer or a cyclic polyolefin copolymer, and the outermost layer comprises a layer containing polypropylene, and which further comprises a resin composition layer comprising a blended product of a propylene polymer and a styrene elastomer, in a state in which the seal layers are laminated on each other such that they face each other. The plastic film of the present invention is molded, so that the seal layer thereof becomes the inner surface thereof. Specifically, the seal layer is allowed to directly come into contact with a liquid-state medicament which is contained in this container.

The plastic container or multilayered film according to the present invention preferably comprises a resin composition layer or a polyethylene layer on the surfaces of both sides of the cyclic polyolefin layer. In addition, for such resin composition layer, a resin composition having a fusion peak temperature only in a temperature range from 120° C. or higher to 170° C. or lower and also having a heat of fusion from 5 J/g or more to 20 J/g or less is preferably used.

The cyclic polyolefin in the cyclic polyolefin layer used for the plastic container or multilayered film according to the present invention is preferably a ring-opening polymer hydrogenation product of dicyclopentadiene or a derivative thereof. Moreover, another preferred embodiment of the cyclic polyolefin is cyclic polyolefin having a glass transition temperature (Tg) of 80° C. to 120° C. A further preferred embodiment of the cyclic polyolefin is cyclic polyolefin having a melt flow rate (230° C., 21.2 N) value of 1 to 20 (g/10 minutes).

As a seal layer used for the plastic container or multilayered film according to the present invention, polypropylene having a melt flow rate (230° C., 21.2 N) value of 1 to 4 (g/10 minutes) is preferable. Furthermore, another preferred embodiment of the seal layer is a seal layer having a bending elasticity of 400 to 600 MPa. A further preferred embodiment of the seal layer is polypropylene having the maximum fusion peak temperature of 125° C. to 135° C. A still further preferred embodiment of the seal layer is propylene having the highest fusion peak temperature of 150° C. to 160° C. The maximum fusion peak temperature and the highest fusion peak temperature used in the present specification will be described. There are cases in which multiple endothermic peaks are observed in differential scanning calorimetry (DSC). The maximum fusion peak temperature means a temperature at which the largest endothermic peak is observed, and the highest fusion peak temperature means a temperature at which the highest temperature peak is observed in a temperature range in which such endothermic peaks are observed.

The outermost layer used for the plastic container or multilayered film according to the present invention is preferably polypropylene having a melt flow rate (230° C., 21.2 N) value of 1 to 4 (g/10 minutes). Another preferred embodiment of the outermost layer is polypropylene having a bending elasticity of 400 to 600 MPa. A further preferred embodiment of the outermost layer is polypropylene having a fusion peak temperature of 160° C. to 170° C.

In the present invention, a multilayered film having a tensile elasticity of 300 MPa or less and a plastic container molded using this multilayered film are preferable.

The plastic container according to the present invention can be preferably sterilized at 115° C. for 30 minutes or more. In another preferred embodiment, the plastic container according to the present invention can be sterilized at 121° C. for 15 minutes or more.

The active ingredient of a liquid-state medicament placed in the plastic container according to the present invention is preferably a pyrazolone derivative represented by the formula (I) as shown below, a physiologically acceptable salt thereof, a hydrate thereof, or a solvate thereof:

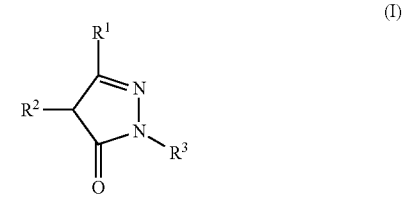

(wherein $R^1$ represents a hydrogen atom, an aryl, an alkyl containing 1 to 5 carbon atoms, or an alkoxycarbonylalkyl containing 3 to 6 carbon atoms in total; $R^2$ represents a hydrogen atom, an aryloxy, an arylmercapto, an alkyl containing 1 to 5 carbon atoms, or a hydroxyalkyl containing 1 to 3 carbon atoms; or $R^1$ and $R^2$ together represent an alkylene containing 3 to 5 carbon atoms; $R^3$ represents a hydrogen atom, an alkyl containing 1 to 5 carbon atoms, a cycloalkyl containing 5 to 7 carbon atoms, a hydroxyalkyl containing 1 to 3 carbon atoms, a benzyl, naphthyl or phenyl, or a phenyl substituted with 1 to 3 identical or different substituents selected from the group consisting of an alkoxy containing 1 to 5 carbon atoms, a hydroxyalkyl containing 1 to 3 carbon atoms, an alkoxycarbonyl containing 2 to 5 carbon atoms in total, an alkylmercapto containing 1 to 3 carbon atoms, an alkylamino containing 1 to 4 carbon atoms, a dialkylamino containing 2 to 8 carbon atoms in total, a halogen atom, a trifluoromethyl, a carboxyl, a cyano, a hydroxyl group, a nitro, an amino, and an acetamide). In another preferred embodiment, the active ingredient of a liquid-state medicament is 3-methyl-1-phenyl-2-pyrazolin-5-one.

The plastic container according to the present invention is preferably in the form of an infusion bag.

Moreover, the plastic container according to the present invention is preferably placed together with an oxygen absorber into a poorly air-permeable container.

When the active ingredient of a liquid-state medicament placed in the plastic container according to the present invention is the pyrazolone derivative represented by the above-described formula (I), a physiologically acceptable salt thereof, a hydrate thereof, or a solvent thereof, a reduction percentage in the content of the active ingredient after the preservation thereof at 60° C. for 4 weeks is preferably 4% or less. On the other hand, a reduction percentage in the content of the active ingredient after sterilization is preferably 4% or less.

BEST MODE FOR CARRYING OUT THE INVENTION

The plastic container and the multilayered film provided by the present invention have a structure in which they comprise at least a cyclic polyolefin layer and a resin composition layer between an outermost layer and a seal layer. The disposition is not limited. Preferably, the resin composition layers or the polyethylene layers are disposed on both sides of the cyclic polyolefin layer. More preferably, the resin composition layers are disposed on both sides of the cyclic polyolefin layer. The resin composition layer that can be disposed on the outermost layer side of this cyclic polyolefin layer may be identical to or different from the resin composition layer that can be disposed on the seal layer side thereof. The same applies to the polyethylene layer.

Polyethylene that constitutes the polyethylene layer used in the present invention may be a copolymer of ethylene with α-olefin such as propylene, 1-butene, 4-methyl-1-pentene or 1-octene, as well as an ethylene homopolymer. In addition, the above-mentioned copolymer may be either a linear or branched copolymer. Moreover, a mixed resin of the ethylene homopolymer and the above-mentioned α-olefin may also be used. Furthermore, regardless of whether it is high-density or low-density, such polyethylene can be selected from a wide range of polyethylenes, as appropriate. From the viewpoint of flexibility and transparency, linear low-density polyethylene is advantageously used.

Specific examples of polyethylene preferably used in the present invention include an ethylene homopolymer (product name: HARMOREC®), an α-olefin copolymer (product name: TOUGHMER®), and an ethylene-1-octene copolymer (product name: MORETEC®). A more preferred example of polyethylene is a mixed resin of HARMOREC® and TOUGHMER®.

The thickness of this polyethylene layer is not particularly limited. It is preferably from 10 μm or more to 150 μm or less.

A resin composition that constitutes the resin composition layer used in the present invention preferably has a fusion peak temperature only in a temperature range from 120° C. or higher to 170° C. or lower and also has a heat of fusion from 5 J/g or more to 20 J/g or less. This resin composition plays a role in improving the adhesion between a cyclic polyolefin polymer or a cyclic polyolefin copolymer and a polyolefin layer and also in improving the flexibility of the multilayered film as a whole. This resin composition has a fusion peak temperature in a temperature range from 120° C. or higher to 170° C. or lower that is derived from the crystalline component of the resin. If such fusion peak temperature is lower than 120° C., a multilayered film resistant to sterilization at 121° C. cannot be constituted. On the other hand, if such fusion peak temperature exceeds 170° C., the molding temperature is too high to produce a multilayered film with good appearance. Moreover, if the heat of fusion is less than 5 J/g, a multilayered film resistant to sterilization at 121° C. cannot be constituted. On the other hand, if it exceeds 20 J/g, the adhesion with a cyclic polyolefin polymer or a cyclic polyolefin copolymer becomes poor, and delamination (delami) easily occurs after completion of the sterilization. As a result, there is a fear that the appearance becomes deteriorated or desired preservability cannot be obtained.

Furthermore, when the resin composition has a fusion peak temperature in a temperature range of lower than 120° C., since a component having such fusion peak is melted during sterilization, the heat resistance of the resin composition is lost, and as a result, deformation, whitening and the like occur on the multilayered film. Examples of a resin having a fusion peak temperature in a temperature range of lower than 120° C. include high pressure method polyethylene or linear low-density polyethylene having a density of 0.93 or less, and an ethylene-α-olefin copolymer having a density of 0.90 or less.

The method for producing the resin composition of the present invention is not particularly limited, as long as the produced resin composition satisfies the above-described conditions, namely, as long as it has a fusion peak temperature only in a temperature range from 120° C. or higher to 170° C. or lower and also has a heat of fusion from 5 J/g or more to 20 J/g or less. For example, there can be applied a method, which comprises: first producing a crystalline propylene homopolymer having a fusion peak temperature in a temperature range from 120° C. or higher to 170° C. or lower, or a propylene-ethylene copolymer containing a small amount of ethylene (approximately 3% by weight or less) by continuous polymerization; and then producing a copolymer consisting of substantially amorphous propylene that does not have a fusion peak temperature in a temperature range from 120° C. or higher to 170° C. or lower and approximately 10% to 20% by weight of ethylene; so as to totally obtain a resin composition having a heat of fusion from 5 J/g or more to 20 J/g or less. There can also be applied a method, which comprises: producing a crystalline propylene homopolymer having a fusion peak temperature in a temperature range from 120° C. or higher to 170° C. or lower, or a propylene-ethylene copolymer of propylene and a small amount of ethylene (approximately 3% by weight or less), and a copolymer of propylene and approximately 10% to 20% by weight of ethylene, separately; and then blending them; so as to totally obtain a resin composition having a heat of fusion from 5 J/g or more to 20 J/g or less.

The above-described method for producing a resin composition by continuous polymerization is disclosed, for example, in JP Patent Publication (Kokai) Nos. 2001-172454 A and 2003-292700 A.

Further, there are produced: a crystalline propylene homopolymer having a fusion peak temperature in a temperature range from 120° C. or higher to 170° C. or lower, a propylene-ethylene copolymer containing a small amount of ethylene (approximately 3% by weight or less); a crystalline propylene homopolymer having a fusion peak temperature in a temperature range from 120° C. or higher to 170° C. or lower, or a propylene-ethylene copolymer containing a small amount of ethylene (approximately 3% by weight or less), produced by continuous polymerization. Thereafter, a copolymer consisting of amorphous or semicrystalline propylene that does not have a fusion peak temperature in a temperature range from 120° C. or higher to 170° C. or lower and approximately 10% to 20% by weight of ethylene is produced to obtain a propylene polymer composition. A propylene copolymer having a fusion peak temperature in a temperature range from 120° C. or higher to 170° C. or lower, selected from among the thus obtained propylene polymer compositions, are blended with a styrene elastomer, so as to obtain a blended product.

The above-described styrene elastomer indicates a hydrogenated derivative of a vinyl aromatic hydrocarbon-conjugated diene block copolymer. It is one or two or more types of hydrogenated derivatives of such block copolymer represented by the formula: a(b-a)n, (a-b)n, or a-b-c (wherein (a) represents a polymer block of monovinyl-substituted aromatic hydrocarbon; (b) represents a random copolymer block of a monovinyl-substituted aromatic hydrocarbon and a conjugated diene, or an elastomeric polymer block of conjugated diene; (c) represents a block of a monovinyl-substituted aromatic hydrocarbon and a conjugated diene, which is a taper block in which the monovinyl-substituted aromatic hydrocarbon is gradually increased; and n represents an integer of 1 to 5).

Examples of a monovinyl aromatic hydrocarbon constituting the above-described polymer block (a), (b) or (c) include styrene, α-methylstyrene, (o-, m-, p-)methylstyrene, 1,3-dimethylstyrene, vinylnaphthalene, and vinylanthracene. Of these, styrene or α-methylstyrene is preferable. As a conjugated diene monomer used in the above-described polymer block (b) or (c), butadiene and/or isoprene are preferable. When butadiene is used as a single conjugated diene monomer to form the polymer block (b) or (c), for the purpose of increasing compatibility with a propylene polymer, after a block copolymer has been hydrogenated so that a double bond has become saturated, there are preferably adopted polymerization conditions in which a 1,2-microstructure accounts for 50% or more (by weight) of the microstructure of polybutadiene. The preferred amount of the 1,2-microstructure is from 50% by weight to 90% by weight. The amount of the polymer block (a) in the hydrogenated block copolymer, or the total amount of the vinyl aromatic compounds of the polymer block (a) and the polymer block (c), is generally from 3% to 30% by weight, and preferably from 5% to 20% by weight. When the amount of the polymer block (a) or the total amount of the vinyl aromatic compounds of the polymer block (a) and the polymer block (c) is less than 3% by weight, the mechanical strength of the obtained composition tends to be deteriorated. On the other hand, when the amount of the polymer block (a) or the total amount of the vinyl aromatic compounds of the polymer block (a) and the polymer block (c) exceeds 30% by weight, the flexibility and transparency of the composition tend to be deteriorated.

The weight average molecular weight of a styrene elastomer (a hydrogenated derivative of a vinyl aromatic hydrocarbon-conjugated diene block copolymer) is generally 100,000 to 550,000, preferably 150,000 to 500,000, and more preferably 200,000 to 450,000, as a value relative to polystyrene measured by gel permeation chromatography. If such weight average molecular weight is less than 100,000, rubber elasticity and mechanical strength tend to be deteriorated. On the other hand, if it exceeds 550,000, viscosity becomes high, and molding processability tends to be deteriorated.

Examples of the above-described styrene elastomer (a hydrogenated derivative of a vinyl aromatic hydrocarbon-conjugated diene block copolymer) include commercially available products such as "KRATON-G" manufactured by Kraton Polymers, "SEPTON" & "HYBRAR" manufactured by Kuraray Co., Ltd., "Toughtech" manufactured by Asahi Kasei Corporation, "Dynaron" manufactured by JSR, and "SIBSTAR" composed of a styrene block and an isobutylene block obtained by cationic polymerization, manufactured by Kaneka Corporation.

As a resin composition having a fusion peak temperature in a temperature range from 120° C. or higher to 170° C. or lower and also having a heat of fusion from 5 J/g or more to 20 J/g or less as obtained above, ZELAS MC729 manufactured by Mitsubishi Chemical Corporation is preferable.

The thickness of this resin composition layer is not particularly limited. It is preferably from 20 μm or more to 120 μm or less, and more preferably from 20 μm or more to 75 μm or less. Moreover, when resin composition layers are disposed on both sides of a cyclic polyolefin layer, the thickness of a resin composition layer on the seal layer side may be identical to or different from the thickness of a resin composition layer on the outermost layer side.

Examples of the cyclic polyolefin polymer or cyclic polyolefin copolymer constituting the cyclic polyolefin layer used in the present invention include: a copolymer of ethylene and dicyclopentadiene; a copolymer of ethylene and a norbornene compound; a ring-opening polymer of a cyclopentadiene derivative; a ring-opening copolymer of various cyclopentadiene derivatives; and a hydrogenation product thereof. Of these, a hydrogenation product of a copolymer of ethylene and a norbornene compound, or a hydrogenation product of a ring-opening (co)polymer of one or more types of cyclopentadiene derivatives is preferably used. A ring-opening polymer hydrogenation product of dicyclopentadiene or a derivative thereof is more preferable.

The above-described resin includes: a polymer having a repeating unit represented by the formula (1) as shown below and a repeating unit represented by the formula (1') as shown below; and a polymer having a repeating unit represented by the formula (2) as shown below.

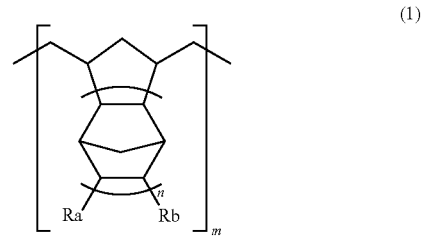

(1)

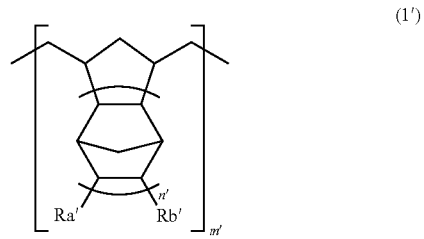

(1')

(wherein, in formulae (1) and (1'), each of Ra, Ra', Rb and Rb' identically or differently represents a hydrogen, a hydrocarbon residue, or a polar group such as a halogen, an ester, a nitrile or a pyridyl; Ra, Ra', Rb and Rb' may bind to one another to form a ring; each of m and m' represents an integer of 1 or greater; and each of n and n' represents an integer of 0 or 1 or greater).

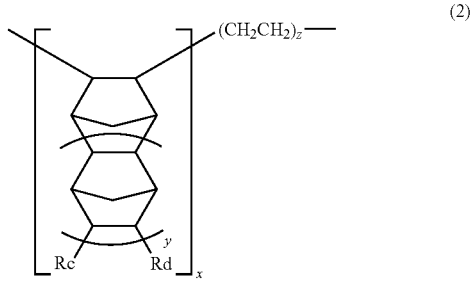

(2)

(wherein, in formula (2), each of Re and Rd identically or differently represents a hydrogen, a hydrocarbon residue, or a polar group such as a halogen, an ester, a nitrile or a pyridyl; $R^3$ and $R^4$ may bind to each other to form a ring; each of x and z represents an integer of 1 or greater; and y represents an integer of 0 or 1 or greater).

The polymer having the repeating units represented by the formulae (1) and (1') is produced by polymerizing one or two or more types of monomers according to a known ring-opening polymerization method, or further by hydrogenating the thus obtained ring-opening polymer according to an ordinary method. Specific examples of such polymer include "ZEONOR (product name; registered trademark)" as a hydrogenated polymer manufactured by Zeon Corporation, and "ARTON (product name; registered trademark)" manufactured by Japan Synthetic Rubber Co., Ltd. The polymer having the structural unit represented by the formula (2) is produced by subjecting one or two or more types of norbornene monomers used as monomers and ethylene to addition copolymerization according to a known method, or further by hydrogenating the obtained product according to an ordinary method. Specific examples of such polymer include "APEL (product name; registered trademark)" manufactured by Mitsui Chemicals, Inc., and "TOPAS (product name; registered trademark)" manufactured by Polyplastics Co., Ltd.

Preferred examples of the cyclic polyolefin polymer or cyclic polyolefin copolymer used in the present invention include "ZEONOA ZEONOR®" and "TOPAS®."

Among the above-exemplified resins containing the above-described polymers having the structural units represented by the formulae (1) and (1') and the formula (2), the hydrogenation products thereof are all saturated polymers. Thus, the hydrogenation products are excellent in terms of heat resistance, transparency and stability, as well as a gas-shielding property and a moisture-shielding property. The cyclic polyolefin polymer used in the present invention has a glass transition temperature ($T_g$) of preferably 70° C. or higher, and more preferably 80° C. to 120° C. Moreover, the range of the molecular weight of the present cyclic polyolefin polymer is preferably 10,000 to 100,000, and more preferably 20,000 to 50,000, relative to a number average molecular weight <Mn> measured by gel permeation chromatography (GPC) using cyclohexane as a solvent. Furthermore, from another viewpoint, the melt flow rate (230° C., 21.2 N) value of the present cyclic polyolefin polymer is preferably 1 to 20 (g/10 minutes). When an unsaturated bond remaining in the molecular chain of cyclic polyolefin is saturated by hydrogenation, the hydrogenation rate is preferably 90% or more, more preferably 95% or more, and particularly preferably 99% or more.

The cyclic polyolefin polymer or the cyclic polyolefin copolymer may be used in the state of a single layer, or may also be used as a mixed resin formed by mixing it with another resin. When the cyclic polyolefin polymer or the cyclic polyolefin copolymer is used as a mixed resin, if the content of the cyclic polyolefin polymer or cyclic polyolefin copolymer in the mixed resin is less than 60% by weight, the effect of preventing the adsorption of an agent is decreased. On the other hand, if the content of the cyclic polyolefin in the mixed resin exceeds 95% by weight, the flexibility of a multilayered film as a whole is decreased. Accordingly, when the cyclic polyolefin polymer or cyclic polyolefin copolymer is used in the form of a mixed resin, the content of the cyclic polyolefin polymer or cyclic polyolefin copolymer is desirably from 60% by weight or more to 95% by weight or less.

Examples of a resin to be mixed with the cyclic polyolefin polymer or cyclic polyolefin copolymer include polyethylene, polypropylene, poly 1-butene, poly 4-methyl-1-pentene, an ethylene-propylene copolymer, a mixture of polypropylene and polyethylene or polybutene, a partially cross-linked product of the aforementioned polyolefin, an ethylene-vinyl acetate copolymer, an ethylene-(meth)acrylic acid ester copolymer, an ethylene-(meth)acrylic acid copolymer, and an ethylene-maleic anhydride copolymer. Of these, preferred examples of such resin include an ethylene homopolymer (product name: HARMOREC®), an α-olefin copolymer (product name: TOUGHMER®), and an ethylene-1-octene copolymer (product name: MORETEC®).

The thickness of the cyclic polyolefin layer is determined within the aforementioned range, while taking into consideration the balance between the effect of preventing the adsorption of an agent and the flexibility of a multilayered film as a whole. If the thickness of the cyclic polyolefin layer is less than 10 μm, the effect of preventing the adsorption of an agent is decreased. On the other hand, if the thickness exceeds 80 μm, the flexibility of a multilayered film as a whole is decreased. The particularly preferred range of the thickness of the cyclic polyolefin layer can be from 10 μm to 50 μm. More preferably, the thickness of the cyclic polyolefin layer can be from 10 μm to 30 μm.

As polypropylene constituting the seal layer used in the present invention, there can be used not only a propylene homopolymer, but also a copolymer produced by copolymerizing propylene with a small amount (preferably 10% by weight or less) of α-olefin such as ethylene or 1-butene, a copolymer produced by multistage polymerization of propylene with α-olefin and the like as disclosed, for example, in JP Patent Publication (Kokai) No. 2001-226435 A. Among others, in order to alleviate the rigidity of the cyclic polyolefin layer and to improve the flexibility of the multilayered film, polypropylene of a relatively flexible grade, having a bending elasticity of 400 to 600 MPa, which has been commonly used as a medical container, is preferably used. Moreover, from another viewpoint, polypropylene having a melt flow rate (230° C., 21.2 N) value of 1 to 4 (g/10 minutes) is preferably used. A specific example of the polypropylene that can be used in the present invention is ZELAS (registered trademark) manufactured by Mitsubishi Chemical Corporation. In particular, ZELAS MC607 having a fusion peak temperature in a temperature range from 125° C. to 135° C. is preferably used. The thickness of the seal layer is not particularly limited. It is preferably from 20 to 120 μm.

A layer comprising polypropylene constituting the outermost layer used in the present invention may be constituted, not only with a propylene homopolymer, but also with a copolymer produced by copolymerizing propylene with a small amount (preferably 10% by weight or less) of α-olefin such as ethylene or 1-butene, a copolymer produced by multistage polymerization of propylene with α-olefin as disclosed, for example, in JP Patent Publication (Kokai) No. 2001-226435 and the like. Moreover, a compound of such homopolymer or copolymer with another polyolefin or resin may also be used. Among others, in order to alleviate the rigidity of the cyclic polyolefin layer and to improve the flexibility of a multilayered film, polypropylene of a relatively flexible grade, having a bending elasticity of 400 to 600 MPa, which has been commonly used as a medical container, is preferably used. Furthermore, from another viewpoint, the melt flow rate (230° C., 21.2 N) value of the outermost layer is preferably set at 1 to 4 (g/10 minutes). A specific example of the polypropylene constituting the outermost layer that can be preferably used in the present invention is ZELAS® manufactured by Mitsubishi Chemical Corporation. In particular, ZELAS MC715 having a fusion peak temperature in a temperature range from 160° C. to 170° C. is preferably used. The thickness of the outermost layer is not particularly limited. It is preferably from 20 to 100 μm.

Hence, a layer containing polypropylene having a high fusion peak temperature is disposed as an outermost layer, and a polypropylene layer having a relatively low fusion peak temperature is disposed as a seal layer, so that the heat-sealing properties of a multilayered film containing a cyclic polyolefin layer are significantly improved, thereby producing a practical container.

Further, from the viewpoint of shock resistance, handling ability during the filling of the container with a medicament, and the moldability of the container, the plastic container and multilayered film of the present invention obtained with the above-described structure desirably has a tensile elasticity of 300 MPa or less.

The active ingredient of a liquid-state medicament that can be filled into the plastic container provided by the present invention is not limited. Preferred examples of such active ingredient include the pyrazolone derivative represented by the formula (I) defined in the present specification, a physiologically acceptable salt thereof, a hydrate thereof, and a solvate thereof.

The compound represented by the formula (I) may also have a structure represented by general formula (I') or (I'') as shown below, as a result of tautomerism. As a matter of convenience, a tautomer is shown by the formula (I) in the present specification. However, the presence of the following tautomers is obvious to persons skilled in the art.

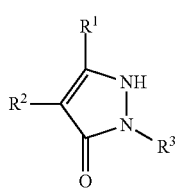
(I')

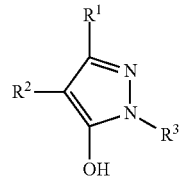
(I'')

In the formula (I), the aryl group represented by $R^1$ may be either a monocyclic or polycyclic aryl group. Examples of such aryl group include: phenyl groups; naphthyl groups; alkyl groups such as a methyl group and a butyl group; alkoxy groups such as a methoxy group and a butoxy group; halogen atoms such as a chlorine atom; and phenyl groups substituted with substituents such as a hydroxyl group. The same applies to aryl portions in other substituents (an aryloxy group, etc.) having such aryl portions.

The alkyl group containing 1 to 5 carbon atoms represented by each of $R^1$, $R^2$ and $R^3$ may be either a linear or branched alkyl group. Examples of such alkyl group include a methyl group, an ethyl group, a propyl group, an isopropyl group, a butyl group, an isobutyl group, a sec-butyl group, a tert-butyl group, and a pentyl group. The same applies to an alkyl portion in another substituent (an alkoxycarbonylalkyl group) having such alkyl portion.

Examples of the alkoxycarbonylalkyl group containing 3 to 6 carbon atoms in total represented by $R^1$ include a methoxycarbonylmethyl group, an ethoxycarbonylmethyl group, a propoxycarbonylmethyl group, a methoxycarbonylethyl group, and a methoxycarbonylpropyl group.

Examples of the alkylene group containing 3 to 5 carbon atoms represented by each of $R^1$ and $R^2$ include a trimethylene group, a tetramethylene group, a pentamethylene group, a methyltrimethylene group, an ethyltrimethylene group, a dimethyltrimethylene group, and a methyltetramethylene group.

Examples of the aryloxy group represented by $R^2$ include a p-methylphenoxy group, a p-methoxyphenoxy group, a p-chlorophenoxy group, and a p-hydroxyphenoxy group. Examples of the arylmercapto group include a phenylmercapto group, a p-methylphenylmercapto group, a p-methoxyphenylmercapto group, a p-chlorophenylmercapto group, and a p-hydroxyphenylmercapto group.

Examples of the hydroxyalkyl group containing 1 to 3 carbon atoms represented by each of $R^2$ and $R^3$ include a hydroxymethyl group, a 2-hydroxyethyl group, and a 3-hydroxypropyl group. Examples of the cycloalkyl group containing 5 to 7 carbon atoms represented by $R^3$ include a cyclopentyl group, a cyclohexyl group, and a cycloheptyl group.

Examples of the alkoxy group containing 1 to 5 carbon atoms as a substituent of the phenyl group represented by $R^3$ include a methoxy group, an ethoxy group, a propoxy group, an isopropoxy group, a butoxy group, and a pentyloxy group. Examples of the alkoxycarbonyl group containing 2 to 5 carbon atoms in total include a methoxycarbonyl group, an ethoxycarbonyl group, a propoxycarbonyl group, and a butoxycarbonyl group. Examples of the alkylmercapto group containing 1 to 3 carbon atoms include a methylmercapto group, an ethylmercapto group, and a propylmercapto group. Examples of the alkylamino group containing 1 to 4 carbon atoms include a methylamino group, an ethylamino group, a propylamino group, and a butylamino group. Examples of the dialkylamino group containing 2 to 8 carbon atoms in total include a dimethylamino group, a diethylamino group, a dipropylamino group, and a dibutylamino group.

A preferably used compound (I) is 3-methyl-1-phenyl-2-pyrazolin-5-one.

The compounds represented by the formula (I) are all known compounds. These compounds can be easily synthesized by persons skilled in the art according to the method described in JP Patent Publication (Kokoku) No. 5-31523 B (1993), and the like.

When the plastic container provided by the present invention is filled with a solution comprising, as an active ingredient, the pyrazolone derivative represented by the above-described formula (I), a physiologically acceptable salt thereof, a hydrate thereof, or a solvent thereof (hereinafter generically referred to as a "pyrazolone derivative," at times), for example, when an infusion bag is prepared by filling the plastic container with such agent, the pyrazolone derivative is dissolved in a solvent (for example, an infusion solution, etc.), to a concentration from approximately 0.06 mg/mL or higher to approximately 2 mg/mL or lower, preferably from approximately 0.1 mg/mL or higher to approximately 0.6 mg/mL or lower, and more preferably approximately 0.3 mg/mL. Thereafter, a pH adjuster is added to the solution, as desired, so as to adjust the pH of the solution. Thereafter, other additives are further added thereto, as desired, so as to prepare an agent filled in the infusion bag.

In order to prepare a liquid-state medicament to be placed in the plastic container of the present invention, all types of ingredients may be used, in addition to the active ingredient, as long as they are commonly used as medicaments. For example, one or two or more types of ingredients arbitrarily selected from among electrolytes, sugars, vitamins, protein amino acids, etc., which are dissolved in any given concentrations in water (for example, distilled water for injection, etc.) may be used. An example of such electrolyte is sodium chloride. These arbitrary ingredients may be used in any given concentration, singly or in combination of two or more types. A preferred example is sodium chloride or the like that has been dissolved in any given concentration in water (for example, distilled water for injection, etc.). In the case of sodium chloride, the content of this ingredient is preferably equivalent to that of a normal saline, namely, approximately 0.9% (W/V). Other than this ingredient, a pH adjuster that is commonly used as a pH adjuster for injection may be used without particular limitations.

The types of other additives that can be used to prepare the liquid-state medicament are not particularly limited, as long as they are commonly used as additives for injections. In the present invention, other preferred additives include pharmaceutical additives described in "*Iyakuhin Tenkabutsu Jiten* (Pharmaceutical Additive Dictionary)," Yakuji Nippo 2000 (edited by the Japan Pharmaceutical Excipients Council), and the like. In general, these additives are mixed at ratios commonly applied to injections. In addition, these additives may be separated, for example, into a stabilizer, a surfactant, a buffer, a solubilizing agent, an antioxidant, an antifoaming agent, an isotonizing agent, an emulsifier, a suspending agent, a preservative, a soothing agent, a resolvent, a solubilization aid, and the like, and may be then used. These additive may be used in combination of two or more ingredients, as desired.

The form of the plastic container of the present invention is not particularly limited, as long as it is hermetically sealable and is able to maintain the sterility of the content. In general, containers such as an infusion bag, a syringe, an ampule and a vial, which are used to contain an injection solution, are preferable. Of these, an infusion bag is particularly preferable. Moreover, in order to confirm the presence or absence of the generation of insoluble foreign matters, these containers are preferably transparent and colorless. However, an opaque, colored container may also be used.

When a liquid-state medicament is placed in the plastic container provided by the present invention, the plastic container can be produced by filling it with the liquid-state medicament and then hermetically sealing it. Moreover, a sterilization operation is carried out on the plastic container in any given process, so as to produce a plastic container maintaining sterility. Furthermore, before filling the container with the medicament, the agent solution may be filtrated with a dust-proof filter (for example, a 0.45-μm methylcellulose membrane, a 0.45-μm nylon 66 membrane, a 0.45-μm polyvinylidene fluoride membrane, etc.), as desired. Specific methods for sterilizing the plastic container of the present invention include a hot water immersion sterilization method, a hot water shower sterilization method, and a high-pressure steam sterilization (autoclave) method. Such hot water immersion sterilization method, hot water shower sterilization method, and high-pressure steam sterilization method are carried out, for example, after the agent solution has been prepared and has been then filled into the plastic container of the present invention. The high-pressure steam sterilization is preferably carried out, for example, under conditions of a temperature of 100° C. to 125° C. for 5 to 40 minutes. The plastic container of the present invention is sterilized, preferably at 115° C. for 30 minutes or longer, and more preferably 121° C. for 15 minutes or longer.

The plastic container and multilayered film provided by the present invention is desirably composed of five or more layers. Specifically, an outermost layer-a resin composition layer-a cyclic polyolefin layer-a resin composition layer-a seal layer is desirably used as a base. By adopting such structure, it becomes possible to sterilize the plastic container of the present invention at 121° C. for 15 minutes or longer, and as a result, a plastic container that has flexibility and high shock resistance and can be easily filled with an agent solution can be produced. Moreover, it is also possible to add any given resin layers between any given layers of the outermost layer-resin composition layer-cyclic polyolefin layer-resin composition layer-seal layer. The any given resin layers added herein include polyolefins such as polypropylene, polyamides, polyesters such as polyethylene terephthalate or polybutylene terephthalate, and ethylene-vinyl alcohol copolymers. Specifically, polyolefins prepared by grafting these polar materials with α,β unsaturated carboxylic acids having adhesiveness therewith, copolymers of carboxylic acids and ethylenes, etc. may be used. Of these, preferred examples of the resin layer include the resin composition layer as described above in the present specification, a polypropylene layer, and a layer containing polypropylene. In order to determine the structure of layers, it is desired to adjust the layer structure, such that the tensile elasticity of the obtained multilayered film can be 300 MPa or less.

When the form of the plastic container provided by the present invention is an infusion bag, it can be produced by sealing the peripheral portions of the multilayered films provided by the present invention according to an ordinary method and molding it into the form of a bag. The thickness of the multilayered film is preferably 500 μm or less, and particularly preferably 200 to 300 μm.

The multilayered film provided by the present invention can be produced by applying various types of conventionally known methods such as a co-extrusion inflation method or a co-extrusion T-die method.

The plastic container of the present invention may be wrapped with a light-shielding material to suppress the permeability of a light with a specific wavelength. The type of a wrapping material used in such wrapping is not particularly limited, as long as it is a commonly used light-shielding wrapping material. Specifically, a bag made of a material for suppressing the permeability of a light with a specific wavelength, a bag made of a light-shielding material such as plastic or aluminum, a shrink wrapping material (for example, a shrink label, etc.) using light-shielding plastic, a blister wrapping material, and the like may be used. By the combined use of these light-shielding materials, their light-shielding properties can be further enhanced.

Production Example of Infusion Bag

Films having the structures shown in Table 1 were produced using a water-cooled type inflation device capable of molding 6 types of 6-layered films. Thereafter, a polyethylene or polypropylene port was deposited on each film, so as to mold a 100-mL infusion bag on which a polyethylene or polypropylene port was deposited. That is to say, the peripheral portions of the multilayered films shown in Table 1 were heat-sealed in a state in which the seal layers were laminated on each other such that they faced each other, so as to produce each infusion bag. In Table 1, films A01, A03, C01 and C02 are the examples of the present invention, and films A02, A04, A05, B01, B02 and B03 are the reference examples of the present invention.

| | Film Composition | | | | | |
|---|---|---|---|---|---|---|
| Outer Layer | 1 | 2 | 3 | 4 (Barrier Layer) | 5 | 6 inner layer |
| A01 | ZELASMC715 30 μm | ZELASMC717 70 μm | | TOPAS9506F-04 10 μm | ZELASMC717 60 μm | ZELASMC607 60 μm |
| A02 | ZELASMC715 30 μm | ZELASMC717 70 μm | | TOPAS9506F-04 10 μm | ZELASMC717 60 μm | MORETECO248Z 50 μm |
| A03 | ZELASMC715 30 μm | ZELASMC717 70 μm | | TOPAS9506F-04/ MORETEC0168N 20 μm | ZELASMC717 60 μm | ZELASMC607 50 μm |
| A04 | MORETEC0168N 30 μm | HARMORECNV325N/ TOUGHMERA4085 70 μm | | TOPAS9506F-04/ MORETEC0168N 20 μm | ZELASMC717 60 μm | ZELASMC607 50 μm |
| A05 | MORETEC0168N 30 μm | HARMORECNV325N/ TOUGHMERA4085 70 μm | | ZEONOR106OR 10 μm | ZELASMC717 60 μm | ZELASMC607 60 μm |
| B01 | | ZELASMC715 70 μm | | TOPAS8007 20 μm | | ZELASMC607 110 μm |
| B02 | | ZELASMC715 70 μm | | ZEONOR106OR 20 μm | | ZELASMC607 110 μm |
| B03 | | ZELASMC715 70 μm | | ZEONOR106OR 30 μm | | ZELASMC607 100 μm |
| C01 | ZELASMC715 20 μm | ZELASMC717 20 μm | ZELASMC729 30 μm | ZEONOR106OR 15 μm | ZELASMC729 75 μm | ZELASMC607 40 μm |
| C02 | ZELASMC715 20 μm | ZELASMC717 35 μm | ZELASMC729 45 μm | ZEONOR106OR 15 μm | ZELASMC729 75 μm | ZELASMC607 40 μm |
| | | | | 2 | | 3 |
| Comparative Example 1 | | ZELAS RT-267A-1 40 μm | | ZELASMC717 120 μm | | ZELAS7023 40 μm |

Furthermore, the plastic container of the present invention may be placed in a poorly air-permeable container. The type of such poorly air-permeable container is not particularly limited, as long as it is produced from a commonly used, poorly air-permeable material. Specifically, it is adequate if such container hardly gives passage to oxygen or nitrogen. Examples of such poorly air-permeable container include an aluminum container and a PET film container formed by silica evaporation. Furthermore, an oxygen absorber may also be placed in such poorly air-permeable container.

EXAMPLES

The present invention will be more specifically described in the following production example, test example, and examples. However, these examples are not intended to limit the scope of the present invention.

In the table, ZELAS® is an olefin (homopolypropylene) thermoplastic elastomer distributed by Mitsubishi Chemical Corporation. ZELAS MC717 and ZELAS MC729 are resin compositions comprising blended products of propylene polymers and styrene elastomers. TOPAS® is a cyclic polyolefin copolymer distributed by Polyplastics Co., Ltd. MORETEC® is a linear low-density polyethylene C8 copolymer produced by copolymerizing ethylene and 1-octene, which is distributed by Prime Polymer Co., Ltd. HARMOREC® is polyethylene distributed by Japan Polyethylene Corporation. TOUGHMER® is an a-olefin copolymer distributed by Mitsui Chemicals, Inc. ZEONOA ZEONOR® is a cyclic polyolefin polymer distributed by Zeon Corporation.

Example 1

A solution obtained by diluting commercially available Radicut® injection 30 mg (manufactured and distributed by Mitsubishi Tanabe Pharma Corporation) with 100 mL of a normal saline was filled into an infusion bag formed with each of various types of films A01 to A05 and Comparative Example 1 shown in Table 1, and it was then sterilized (115° C., 30 minutes). The content of a main component (Edaravone) was measured before and after the sterilization. The results are shown in Table 2. In the case of using a film comprising a cyclic polyolefin polymer or a cyclic polyolefin copolymer as a barrier layer, a significant reduction in the content of the component was not observed after the sterilization. On the other hand, in the case of using a film constituted only with polypropylene (ZELAS® RT-267A-1, MC717, 7023), a reduction in the content of the component was observed after sterilization.

TABLE 2

Medicament adsorption on bag during sterilization in case of using COP or COC as barrier layer

|  | After filling | After sterilization | Reduction rate in content |
|---|---|---|---|
| Film A01 | 101.1 | 99.1 | 2.0 |
| Film A03 | 101.1 | 98.3 | 2.8 |
| Comparative Example 1 | 102.7 | 98.4 | 4.3 |

Test Example 1

A solution obtained by diluting commercially available Radicut® injection 30 mg (manufactured and distributed by Mitsubishi Tanabe Pharma Corporation) with 100 mL of a normal saline was filled into an infusion bag formed with each of various types of films A05 and B01 to B03 shown in Table 1, and it was then sterilized (115° C., 30 minutes). The content of a main component (Edaravone) was measured before and after the sterilization. The results are shown in Table 3. Films comprising a cyclic polyolefin polymer or a cyclic polyolefin copolymer as a barrier layer were able to suppress the adsorption of the component during the sterilization at almost same levels. If the thickness of such cyclic polyolefin polymer was 10 μm or more, it sufficiently exhibited its functions.

TABLE 3

|  | After filling | After sterilization | Reduction rate in content |
|---|---|---|---|
| Difference in medicament adsorption on bag in case of using COP or COC as barrier layer | | | |
| Film B01 | 103.1 | 100.2 | 2.9 |
| Film B02 | 103.1 | 101.7 | 1.4 |
| Influence of thickness of COP on medicament adsorption | | | |
| Film A05 | 97.9 | 96.1 | 1.8 |
| Film B02 | 97.9 | 97.7 | 0.2 |
| Film B03 | 97.9 | 97.3 | 0.6 |

Example 2

A solution obtained by diluting commercially available Radicut® injection 30 mg (manufactured and distributed by Mitsubishi Tanabe Pharma Corporation) with 100 mL of a normal saline was filled into an infusion bag formed with each of various types of films of C01, C02 and Comparative Example 1 shown in Table 1, and it was then sterilized (115° C., 30 minutes). Thereafter, a severe test (60° C., 4 weeks) was carried out on each sample wrapped with a second wrapping material containing AGELESS as an oxygen absorber and having a suppressed gas permeability, which had been formed by silica evaporation. As shown in Table 4, in the case of the bag of Comparative Example 1, a reduction in the content of the component was observed over time. However, such reduction in the content of the component was not observed in the case of the bags of C01 and C02.

TABLE 4

Severe stability test of bags containing COP as barrier layers (60° C.)

|  | After filling | After sterilization | Week 1 | Week 2 | Week 4 |
|---|---|---|---|---|---|
| Film C01 | 97.9 | 96.4 | 96.2 | 97.3 | 98.2 |
| Film C02 | 97.9 | 96.1 | 96.7 | 96.9 | 97.5 |
| Comparative Example 1 | 102.7 | 98.4 |  | 91.0 | 90.9 |

In the table, in the case of films C01 and C02, the content of Edaravone after 4 weeks have passed is higher than the content of Edaravone after completion of the sterilization. This is because the solvent (water) in the bag was evaporated to outside of the bag during the storage at 60° C.

INDUSTRIAL APPLICABILITY

According to the present invention, a plastic container suitable for containing a liquid-state medicament and a multilayered film used to produce this container can be provided. The plastic container and the multilayered film obtained by the present invention are able to suppress a reduction in the content of the active ingredient of a medicament contained therein, do not cause delamination due to high-pressure steam sterilization and long-term conservation, and are excellent in terms of shock resistance, handling ability during the filling of the container with a medicament, and the moldability and transparency of the container.

The invention claimed is:
1. A plastic container containing a solution comprising, as an active ingredient, 3-methyl-1-phenyl-2-pyrazolin-5-one, wherein the container comprises:
a multilayered film having six or more layers, wherein the six or more layers are:
an innermost heat-sealable seal layer consisting essentially of polypropylene,
a first resin composition layer disposed on the innermost heat-sealable seal layer consisting essentially of a resin composition comprising a blended product of a propylene polymer and a styrene elastomer,
a cyclic polyolefin barrier layer disposed on the first resin composition layer consisting of a polymer consisting of repeating units represented by the formula (1) and repeating units represented by the formula (1'):

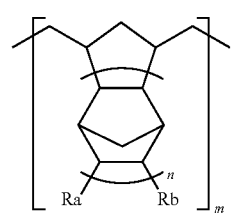

(1)

-continued

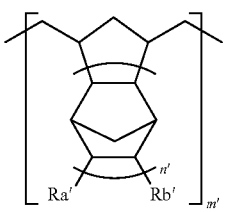

(1')

wherein each of Ra, Ra', Rb and Rb', identically or differently, represents a hydrogen, a hydrocarbon residue, a halogen, an ester, a nitrile or a pyridyl; or Ra and Rb may bind to one another to form a ring; or Ra' and Rb' may bind to one another to form a ring; each of m and m' represents an integer of 1 or greater; and each of n and n' represents an integer of 0 or 1 or greater, two or more additional resin composition layers disposed on the cyclic polyolefin barrier layer consisting essentially of a resin composition comprising a blended product of a propylene polymer and a styrene elastomer, and an outermost layer disposed on the additional resin composition layers consisting essentially of a polypropylene layer;

wherein the plastic container is molded by heat sealing peripheral portions of the multilayered films.

2. The plastic container according to claim 1, wherein the cyclic polyolefin of the cyclic polyolefin barrier layer is a ring-opening polymer hydrogenation product of dicyclopentadiene or a derivative thereof.

3. The plastic container according to claim 1, wherein the cyclic polyolefin barrier layer has a glass transition temperature (Tg) of 80° C. to 120° C.

4. The plastic container according to claim 1, wherein the melt flow rate (230° C., 21.2 N) value of the cyclic polyolefin barrier layer is 1 to 20 (g/10 minutes).

5. The plastic container according to claim 1, wherein the melt flow rate (230° C., 21.2 N) value of the seal layer and/or the outermost layer is 1 to 4 (g/10 minutes).

6. The plastic container according to claim 1, wherein the maximum fusion peak temperature of the seal layer is 125° C. to 135° C.

7. The plastic container according to claim 1, wherein the highest fusion peak temperature of the seal layer is 150° C. to 160° C.

8. The plastic container according to claim 1, wherein the fusion peak temperature of the outermost layer is 160° C. to 170° C.

9. The plastic container according to claim 1, which can be sterilized at 115° C. for 30 minutes or more.

10. The plastic container according to claim 1, which can be sterilized at 121° C. for 15 minutes or more.

11. The plastic container according to claim 1, which is in the form of an infusion bag.

12. The plastic container according to claim 1, which is placed together with an oxygen absorber into a poorly air-permeable container.

* * * * *